United States Patent

Rühl et al.

[11] Patent Number: 5,603,813
[45] Date of Patent: Feb. 18, 1997

[54] PURIFYING DISTILLATION OF VINYL FORMATE

[75] Inventors: Thomas Rühl, Frankenthal; Marc Heider, Neustadt; Jochem Henkelmann; Ralf-Thomas Rahn, both of Mannheim; Harald Rust, Neustadt, all of Germany

[73] Assignee: BASF Aktiengesellschaft, Ludwigshafen, Germany

[21] Appl. No.: 510,568

[22] Filed: Aug. 2, 1995

[30] Foreign Application Priority Data

Aug. 10, 1994 [DE] Germany ............... 44 28 303.2

[51] Int. Cl.$^6$ ............... B01D 3/00; C07C 51/44
[52] U.S. Cl. ............... 203/74; 203/15; 203/17; 203/44; 203/77; 562/531; 568/460

[58] Field of Search ............... 203/11, 17, 15, 203/44, 73, 74, 76, 77, 79, 81, 83, 85, 91, 93, 92; 562/531; 568/460

[56] References Cited

U.S. PATENT DOCUMENTS

| | | |
|---|---|---|
| 2,329,644 | 9/1943 | Owens . |
| 3,965,081 | 6/1976 | Strecker et al. ............... 526/9 |
| 5,053,552 | 10/1991 | Mori et al. ............... 568/460 |
| 5,196,578 | 3/1993 | Kuragano et al. ............... 562/531 |

Primary Examiner—Christopher Kim
Attorney, Agent, or Firm—Keil & Weinkauf

[57] ABSTRACT

Vinyl formate containing formic acid, acetaldehyde and water following synthesis is separated from formic acid and water in a first distillation stage and from acetaldehyde in a second stage to give pure vinyl formate.

3 Claims, No Drawings

PURIFYING DISTILLATION OF VINYL FORMATE

The invention relates to a process for the purification, by distillation, of vinyl formate, in which vinyl formate containing formic acid, acetaldehyde, and water following synthesis is separated from these by-products by distillation.

During the synthesis of vinyl formate from formic acid and acetylene there is also formed acetaldehyde due to thermal decomposition of ethylidene bisformate produced as an intermediate. In polymerizations, acetaldehyde acts as a modifier and leads to short polymerization cycles and to short chain lengths. Thus when it is desired to synthesize polymer chains of vinyl formate the acetaldehyde must be removed as completely as possible from the crude reaction solution. Experiments to separate the products from each other by simple distillation have led to acetaldehyde-containing vinyl formate fractions despite distinct boiling point differences between the educts (acetaldehyde 21° C., vinyl formate 47° C., formic acid 101° C.). This is due to the fact that, at the base of the distilling apparatus, ethylidene bisformate is formed from formic acid and vinyl formate, which in turn forms acetaldehyde.

Thus the object of the invention is to provide a process for the purification, by distillation, of vinyl formate.

This object has been achieved by a process of the type defined above, in which, according to the invention, the vinyl formate is separated from formic acid and water, in a first distillation stage, and from acetaldehyde in a second stage.

Further details and advantages of the process of the invention are evident from the following detailed description of one embodiment.

The vinyl formate discharged from the synthesis plant with all of the by-products is subjected, continuously or batchwise, to a two-stage distillation procedure. In the first stage formic acid and water are separated. The distillation column used for this purpose is, for example, a tray column or packed column having from 1 to 15 trays and preferably from 5 to 10 trays, using the following operating parameters:

pressure range: 800–1020 mbar, preferably 950–1013 mbar temperature at the bottom: 100°–130° C., preferably 110°–125° C.

temperature at the top: 30°–60° C., preferably 35°–50° C.

reflux ratio: 1:1 to 10:1, preferably 2:1 to 5:1

Acetaldehyde and vinyl formate thus pass as overheads to a second distillation column, whilst formic acid and water collect at the bottom of the first column.

The second column, which is preferably also a tray column having from 15 to 45 trays, preferably 20 to 35 trays, serves to separate acetaldehyde and vinyl formate and operates with the following parameters:

pressure range: 800–1020 mbar, 950–1013 mbar temperature at the bottom: 80°–120° C., preferably 95°–110° C.

temperature at the top: 10°–25° C., preferably 15°–21° C.

temperature at the branch outlet: 35°–80° C., preferably 45°–70° C.

reflux ratio: 1:1 to 30:1, preferably 5:1 to 20:1

The feed to the second column must preferably be free from formic acid, since this is responsible for the formation of acetaldehyde from vinyl formate.

Experiments on a commercial scale have shown that vinyl formate obtained in accordance with the process of the invention has a purity of 99.99%.

EXAMPLE

A crude effluent having the following composition: 55% of vinyl formate, 40% of formic acid, and 5% of acetaldehyde, is distilled under standard pressure in a bubble-cap column having 11 trays at an evaporator temperature of 115° C. This causes acetaldehyde and vinyl formate to distill off at the top in a ratio of 7:93. Formic acid and water collect at the bottom of the column.

The acetaldehyde/vinylformate fraction is then distilled in a bubble-cap column having 45 trays and an evaporator temperature of 100° C. Vinyl formate remains at the bottom of the column and has a purity of 99.99% at a distillation yield of 98% over both stages.

We claim:

1. A process for separating vinyl formate from a synthesis mixture containing vinyl formate, formic acid, acetaldehyde and water, which process comprises: distilling the synthesis mixture in a first column to remove an acetaldehyde and vinyl formate fraction from the formic acid and water, passing the acetaldehyde and vinyl formate fraction to a second distillation column, and distilling off the acetaldehyde from the thus purified vinyl formate.

2. A process as defined in claim 1, wherein the distillations are carried out under a reduced pressure of from 800 to 1020 mbar.

3. A process as defined in claim 1, wherein the distillations are carried out under a reduced pressure of from 950 to 1013 mbar.

* * * * *